United States Patent [19]

Winters

[11] Patent Number: Plant 7,608

[45] Date of Patent: Jul. 30, 1991

[54] HIBISCUS PLANT NAMED 'SWEET CAROLINE'

[76] Inventor: Harold F. Winters, 10717 Kinloch Rd., Silver Spring, Md. 20903

[21] Appl. No.: 513,493

[22] Filed: Apr. 20, 1990

[51] Int. Cl.[5] ..... A01H 5/00

[52] U.S. Cl. ..... Plt./54

[58] Field of Search ..... Plt./54, 67.8

*Primary Examiner*—Howard J. Locker

[57] ABSTRACT

An herbaceous perennial Hibiscus plant named 'Sweet Caroline' having numerous broadly campanulate flowers of bright pink with petal edges ruffled and partially reflexed, buds of similar color having the exposed petal edge reflexed, and, upright plants branching apically with shallowly lobed basal and entire upper leaves of a medium green color.

1 Drawing Sheet

The present invention comprises a new and distinct cultivar of Rosemallow (herbaceous perennial) Hibiscus hybrides hereinafter referred to by the cultivar name 'Sweet Caroline'.

The new cultivar is of value for its floral display, produced from mid-July until frost, depending somewhat upon environmental conditions and culture, and for the landscape value of the entire plant.

'Sweet Caroline' originated as a seedling selection from the second generation progeny of a cross pollination between (1) a breeding line derived from crossing Hibiscus 'Super Clown' with *H. palustris* collected from the wild, and (2) a breeding line derived from self pollinating Hibiscus 'Plume'. It was selected by Harold F. Winters in July 1985 from a seedling population grown on his property near Ridgely, Caroline County, Md. He is the owner of the clone and controls all propagations of it.

The selection has maintained its distinguishing characters through succeeding propagations of vegetative cuttings and by division of the rootstocks.

BACKGROUND OF THE NEW PLANT

The objective of this breeding program was primarily to develop a plant with the following characteristics:

(a) Decorative foliage of a pleasing shade of green that blends well with that of other perennial plants and ornamental shrubs.

(b) Attractive pink flower buds that open into flowers that are distinctive for the pink color and form, that are well posed on the plant and that remain open for most of the day.

(c) A plant of medium size and vigor, of good form and habit, and with good landscape quality.

The breeding program which produced 'Sweet Caroline' extended over a period of some 20 years. The pollen parent was an unnamed hybrid seedling resulting from multiple crossings of *Hibiscus coccineus, Hibiscus militaris, Hibiscus moscheutos* and *Hibiscus palustris.* The seed parent was an unnamed seedling selected from a self-pollinated progeny of Hibiscus 'Plume'. Each generation of seedlings was rigidly screened for the above named characteristics. Only those which most nearly met all standards were selected as parents of succeeding generations.

The new plant produced its first flowers in the summer of 1985. It was selected for testing and propagation because of its beautiful pink flower buds and flowers. Asexual propagation of this new plant by vegetative cuttings and by division of the rootstocks was carried on at Ridgely, Md. These asexually-propagated progeny exhibit flower and plant characteristics exactly like those of the parent plant.

ILLUSTRATIONS OF THE NEW PLANT

Flower bud, flower, foliage, and, to some extent, plant characteristics of the new plant are shown in the attached illustrations. The flower colors are as true as it is possible to secure through color photography.

DESCRIPTION OF THE NEW PLANT

A detailed description of the new variety follows. The color terminology is in accordance with *The Royal Horticultural Society Color Chart* (abbreviated by the initials R.H.S. and followed by the color code number) or by ordinary American terminology for color.

The Plant

Hibiscus 'Sweet Caroline' is an herbaceous perennial. The stems die back to ground level each winter, but are replaced by new growths each spring. Annually, the plants attain a height of 1.2 to 1.8 m. (4 to 6 ft.), depending upon exposure to sunlight, soil fertility and soil moisture. The stems are stout at the base becoming slender and branching toward the apices. They are light green when young but develop an overcast of red-purple (R.H.S. 186-C) when mature, where exposed to direct sunlight. At maturity the plants are upright and slightly spreading.

The leaves are abundant, glabrous or nearly so on the upper surface, slightly dull and somewhat pubescent on the lower. In shape they are ovate to broadly ovate. The lower stem leaves usually have two short side lobes, but the upper leaves are entire. Leaves measure up to 17 cm. (6.7 in.) long and 13 cm. (5.1 in.) broad, those toward the stem apices being smaller. The leaf apex is acute, margins are finely to coarsely dentate. In color the young leaves are light green (R.H.S. 147B), maturing to medium green (R.H.S. 147A), with the underside light green (R.H.S. 147C). The intensity of green coloring is dependent upon the nitrogen nutrition of the plant.

The Flower

Hibiscus 'Sweet Caroline' starts to flower each year in mid-July. Flowering is profuse for about one month then continues at a diminished rate until frost. The flowers are borne singly in the axils of the leaves, beginning about midway of the stems and progressing upward.

Each blossom is of one day's duration. In this cultivar the flower buds contribute considerably to the over-all display. The buds begin to show color about three days before anthesis. On the day before anthesis the buds have elongated to about 6 cm. (2.4 in.) and the exposed edge of each petal is reflexed and exhibits color as in the mature flower. This behavior is similar to that of many expanding rose buds. It has not been observed to the same extent in other hibiscus clones.

The broadly campanulate corolla measures about 21 cm. (8.3 in.) wide. It is composed of five widely flared, distinct, obliquely orbicular, overlapping petals. The outer margins of the petals are irregularly ruffled and partly reflexed which gives an attractive irregular outline to the flower perimeter. When pressed flat the petals measure 10–11 cm. (4 to 4.3 in.) long, 13 cm. (5.1 in.) wide.

The over-all aspect of flower color is bright pink, but close examination reveals considerable variation in shading. The broad petals are of Neyron Rose (R.H.S. 55B to R.H.S. 55C) with slightly darker veins (R.H.S. 55A). The partially reflexed margins may be as dark as Spinel Red (R.H.S. 54A). These colors shade darker toward the flower center to form an eye zone about 2.5 cm. (1 in.) in diameter of Cardinal Red (R.H.S. 53B).

A prominent staminal column protrudes from the point of petal attachment. It is white, about 6.5 cm. (2.6 in.) long and bears numerous short-stalked white stamen along the basal two-thirds. When released, the pollen is of a greyed-white color (R.H.S. 156C).

A slender white style terminates the staminal column. Usually it is bent upwards from the point of emergence from the stamens. It is about 2.5 cm. (1 in.) long and is divided into five branches apically. Each branch terminates in a granular capitate stigmatic lobe of Neyron Rose color (R.H.S. 55A).

Each flower is subtended by a 3.5 cm. (1.4 in.) long calyx, connate at the base and with five acute lobes of a medium green color that are adnate for about one-half their length.

Seven or eight slender, 3 cm. (1.2 in.) long bractlets of a medium green color form a whorl about the base of the calyx. There are no stipules.

The medium-green peduncles are slender but stiff, 6 to 8 cm. (2.4 to 3.1 in.) in length.

I claim:

1. A new and distinctive cultivar of Hibiscus plant named 'Sweet Caroline', substantially as herein shown and described, having pink flowrs and buds with reflexed petal margins, a plant suitable for landscape use that blooms from midsummer until frost.

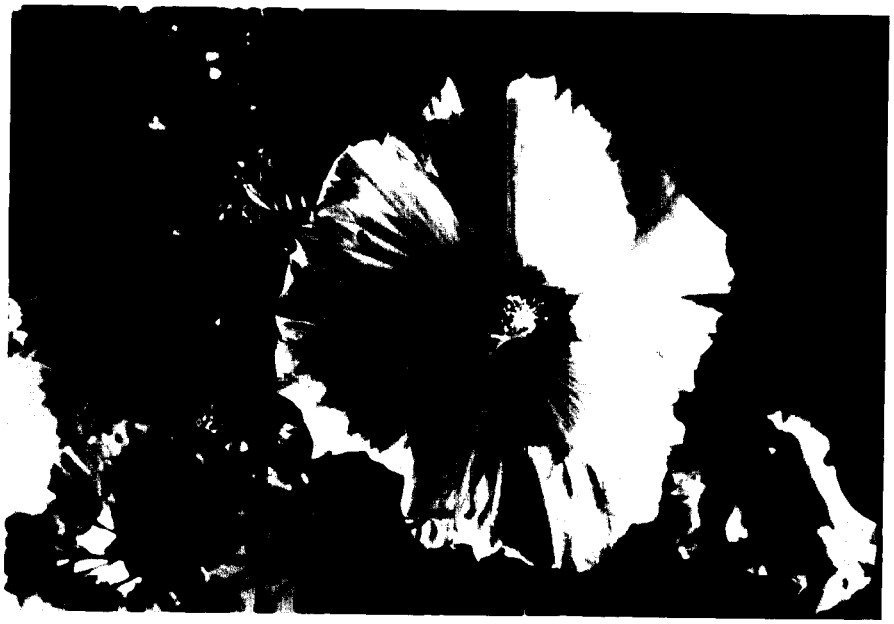
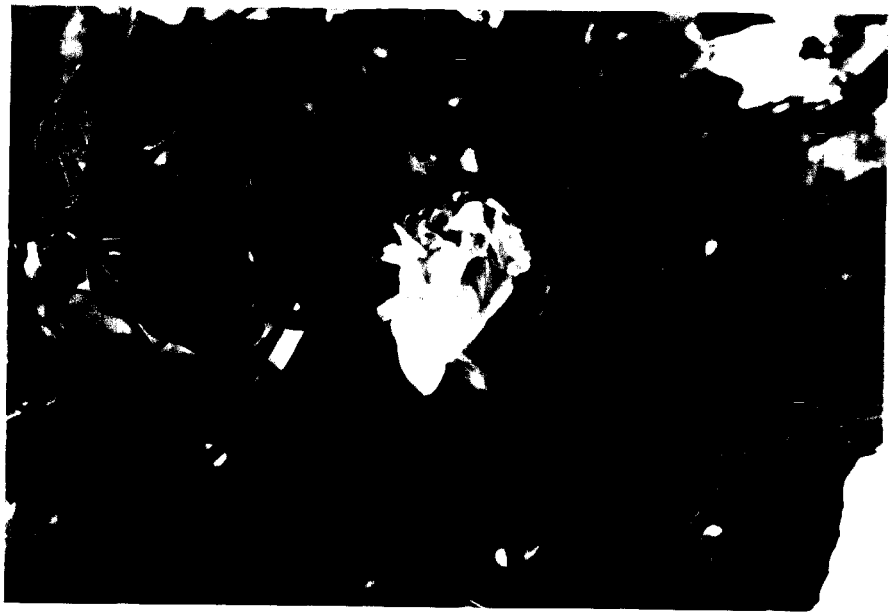

* * * * *